United States Patent [19]

Merk et al.

[11] Patent Number: 4,479,820
[45] Date of Patent: Oct. 30, 1984

[54] USE OF POLYCONDENSATION PRODUCTS FROM ACROLEIN AND FORMALDEHYDE AS BIOCIDE

[75] Inventors: Wolfgang Merk, Limeshain; Karl-Heinz Rink, Hanau, both of Fed. Rep. of Germany

[73] Assignee: Degussa Akteingesellschaft, Frankfurt, Fed. Rep. of Germany

[21] Appl. No.: 464,863

[22] Filed: Feb. 8, 1983

[30] Foreign Application Priority Data

Feb. 16, 1982 [DE] Fed. Rep. of Germany ....... 3205487

[51] Int. Cl.³ .............................................. C02F 1/50
[52] U.S. Cl. ........................................ 71/67; 162/161; 210/764; 424/334
[58] Field of Search .................... 71/67; 162/161, 190; 210/732, 735, 764; 422/36; 424/334; 528/245, 246, 248, 259, 266, 270

[56] References Cited

U.S. PATENT DOCUMENTS

| 2,428,329 | 9/1947 | Ham et al. | 210/764 |
| 3,006,807 | 10/1961 | Legator | 162/161 |
| 3,052,594 | 9/1962 | Baker | 71/67 |
| 3,250,667 | 5/1966 | Legator | 71/67 |
| 4,040,977 | 8/1977 | Eggensperger et al. | 422/36 |

FOREIGN PATENT DOCUMENTS

| 965348 | 4/1975 | Canada | 71/67 |
| 1083545 | 6/1960 | Fed. Rep. of Germany | 528/270 |
| 873800 | 7/1961 | United Kingdom | 162/161 |

Primary Examiner—Peter Hruskoci
Attorney, Agent, or Firm—Cushman, Darby & Cushman

[57] ABSTRACT

There are employed as biocides for aqueous systems water soluble low molecular weight polycondensation products which are produced from acrolein and formaldehyde in the molar ratio between 1:1 and 1:10 in aqueous or aqueous-organic medium in the presence of a basic catalyst. The condensation reaction can also be carried out in the additional presence of water soluble mono- or polyhydric alcohols and/or acid amides.

15 Claims, No Drawings

USE OF POLYCONDENSATION PRODUCTS FROM ACROLEIN AND FORMALDEHYDE AS BIOCIDE

BACKGROUND OF THE INVENTION

The present invention is directed to the use of polycondensation products which are produced by the condensation of acrolein and formaldehyde in a molar ratio between 1:1 and 1:10 in aqueous or aqueous-organic medium in the presence of a basic catalyst as biocides for aqueous systems.

It is already known to use acrolein as a biocide for aqueous systems, for example, to prevent growth of algae in water circulation and to reduce the biological bacterial count. The biocide effectiveness of acrolein indeed is good, its use, however, also has considerable disadvantages, above all, because of its extraordinarily pungent odor even in the slightest concentration and on account of its low flash point. Also there is considerable difficulty in distributing small amounts of acrolein homogeneously in water within a short time even though acrolein is soluble to about 18% in water.

SUMMARY OF THE INVENTION

It has now been found that the disadvantages associated with the use of acrolein as a biocide can be avoided by employing instead low molecular weight water soluble polycondensation products of acrolein and formaldehyde. The use of these polycondensation products proceeds very simply because they are readily dilutable with water. Besides they are substantially less odoriferous than acrolein. Their effectiveness as biocides reaches about that of acrolein and in certain cases it even exceeds the effectiveness of acrolein. A further advantage is that the polycondensation products used according to the invention show no slackening in their biocidal activity with time, while acrolein dissolved in water in the course of several weeks undergoes an aging or chemical change which is associated with a considerable reduction of the biocidal activity.

The polycondensation products used according to the invention are produced by condensation of acrolein and formaldehyde in a molar ratio between 1:1 and 1:10, preferably between 1:2 and 1:4, in aqueous or aqueous-organic medium in the presence of a basic catalyst.

Suitable basic catalysts for example are the hydroxides or carbonates of sodium, potassium and ammonium, e.g. sodium hydroxide, potassium hydroxide, ammonium hydroxide, sodium carbonate, potassium carbonate, and ammonium carbonate. Especially suited are primary, secondary, or tertiary amines, e.g. methylamine, ethylamine, diethylamine, triethylamine, butylamine. Preferably piperidine is used. The catalysts are employed in an amount between 0.1 and 5 weight percent, preferably between 0.5 and 1 weight percent, based on the weight of acrolein and formaldehyde employed.

The formaldehyde can be employed either in the form of an aqueous formaldehyde solution or in the form of paraformaldehyde, followed by addition of water.

In many cases it is advantageous to carry out the condensation reaction in the additional presence of water soluble mono- or polyhydric alcohols and/or acid amides. The alcohols and acid amides can be employed in amounts up to one mole per mole of acrolein employed and are incorporated at least partially into the polycondensation product formed. Suitable alcohols for example, are methanol, ethanol, n-propanol, isopropyl alcohol, ethylene glycol, 1,4-butanediol, triethylene glycol and other water soluble polyglycols, e.g. diethylene glycol, dipropylene glycol. Especially suitable is allyl alcohol. Suitable amides for example are acetamide, urea or caprolactam. Especially suitable is formamide.

The condensation reaction is strongly exothermic. Relatively small production charges can be carried out in such manner that the reactants are mixed and the catalyst added, with larger production charges, however, it is advisable to have present only a part of the reactants or water or an alcohol together with the catalyst and to slowly add the remainder of the reactants portionwise or continuously with such speed that the heat of reaction liberated can be led off without problem.

For the use as biocide according to the invention the polycondensation products formed in the condensation reaction are employed directly in the form of the aqueous or aqueous-organic solution obtained. The concentrations in the use as a biocide, calculated as solid, are in the range between about 1 and about 500 ppm.

Naturally larger concentrations than 500 ppm are also usable without doing anything further but are not meaningful for economical reasons. Customarily the polycondensation products are used in a concentration between 5 and 50 ppm. Only if strongly polluted aqueous systems, e.g. circulating water contaminated with algae and microorganisms is treated for the first time, it is recommended that a higher dosage, for example, in the range between 100 and 200 ppm be used. When the sought success of the treatment has been established the concentration can then again be reduced accordingly.

The polycondensation products used in the invention prevent growth of algae, destroy microorganisms living in water and contribute to the reduction in the number of germs. They can be employed in circulating water, e.g. in power plants or refineries as well as in irrigation channels for areas used for agricultural purposes. In the following examples, there is explained in more detail the production of the polycondensation products used in the invention and the testing of their biocidal activity. Unless otherwise indicated all percentages are by weight.

The process of the invention can comprise, consist essentially of, or consist of the stated steps with the recited materials.

EXAMPLE 1

34.5 cc of acrolein (purity of 96%, density 0.845)=0.5 mole were mixed with 72.6 cc of an aqueous formaldehyde solution (content 37%, density 1.116)=1 mole and diluted with 75 cc of water. At room temperature there was added under stirring 0.5 cc of piperidine. The reaction mixture within a scant minute reached a temperature of 90° C. It was stirred at this temperature for a further 30 minutes and then cooled to room temperature.

The thus obtained polycondensation product of acrolein and formaldehyde in the molar ratio of 1:2 was added in concentrations of 100 ppm, 20 ppm and 5 ppm to algae cultures (*Chlorella kessleri*), which had been cultivated in 1 liter glass beakers in a special algae nutrient solution and whose time of growth with optimum conditions after innoculation with test germs had amounted to about 1 to 2 weeks.

In order to compare the biocidal activity with that of acrolein, the stated concentrations were only calculated on the content of acrolein in the polycondensation product.

After a time of action of 3 to 4 days at room temperature at all three concentrations there was noticed damage to the algae. At 100 ppm the algae growth was totally stopped (activity very good), at 20 ppm the activity was good, while at 5 ppm the activity was still sufficient.

In comparison thereto acrolein freshly dissolved in water at 100 ppm had a very good activity, likewise at 20 ppm, but at 5 ppm the activity was insufficient.

In repeating the experiment with the acrolein solution after 4 weeks or 8 weeks/at 100 ppm, the activity remained the same, at 20 ppm, however, it had fallen off to insufficiency. The solution of the polycondensation product on the contrary after 4 or 8 weeks showed an unchanged activity.

EXAMPLE 2

There were present in a 250 ml round bottom flask equipped with a stirrer 72.6 cc of an aqueous formaldehyde solution (content 37%, density 1.116)=1 mole and 0.5 cc of piperidine and preheated to 70° C. There were dropped in with stirring a homogeneous mixture of 34.5 cc of acrolein (purity 96%, density 0.845)=0.5 mole and a further 72.6 cc of the above formaldehyde solution=1 mole at such speed that a maximum temperature of 80° C. was reached but not exceeded. There was needed a time of 3 minutes for this. Subsequently the mixture was stirred for another hour at 80° C. and then cooled to room temperature.

The thus obtained polycondensation product of acrolein and formaldehyde in the molar ratio 1:4 analogous to Example 1 was again tested in concentrations of 100 ppm, 20 ppm and 5 ppm for its effect on algae cultures, whereby again the concentrations were calculated only on the acrolein content. Within 3 days there was observed with all three concentrations a complete death of the algae cultures.

The testing of efficiency was repeated with the difference that the calculation of concentration was not based on the acrolein content but the total solids content. In this case there resulted a very good activity at 100 ppm and 20 ppm and a still sufficient activity at 5 ppm.

In order to test whether the polycondensation products used in the invention also maintained their effectiveness at elevated temperatures, the above-recited polycondensation product of acrolein and formaldehyde in the molar ratio 1:4 was first heated in an autoclav at 130° C. and then tested again for its biocidal activity. Just as before it showed that at 100 ppm there was present a very good activity, the algae cultures were killed within 3 to 4 days, while at 20 ppm the activity declined to satisfactory to sufficient values.

EXAMPLE 3

60 grams of paraformaldehyde=2 mole, 0.5 gram of piperidine and 80 grams of water were present in a 250 ml round bottom flask equipped with stirrer and reflux condenser and heated to 70° C. Within 3.5 minutes under stirring there were dropped in 34.5 cc of acrolein (purity 96%, density 0.845)=0.5 mole. Subsequently the mixture was stirred for another hour at 80° C. and then cooled to room temperature.

The thus obtained polycondensation product of acrolein and formaldehyde in the molar ratio 1:4 showed the same activity as that produced and tested in Example 2.

Additionally the effectiveness of the polycondensation product was tested against molds and bacteria.

With the *Aspergillus niger* type of mold the minimum concentration for checking the growth was around 125 ppm. In comparison thereto acrolein has a value of 80 ppm.

With the *Bacillus subtilis* type of bacteria there were needed 20 ppm in order to check the growth of germs. This amount was also needed with acrolein in order to produce a comparable effect.

With the *Staphylococcus albus* type of bacteria there were needed 40 ppm to check the growth of the germs. In this case there was needed with acrolein double the concentration, namely 80 ppm to obtain a corresponding effect.

EXAMPLE 4

There were present in a 250 ml round bottom flask provided with a stirrer 36.3 cc of an aqueous formaldehyde solution (content 37%, density 1.116)=0.5 mole, 50 cc of water and 0.5 cc of piperidine and the mixture preheated to 70° C. There were dropped in with stirring a homogeneous mixture of 34.5 cc of acrolein (purity 96%, density 0.845)=0.5 mole and a further 72.6 cc of the above formaldehyde solution=1 mole at such speed that the temperature of 80° C. was not exceeded. There was needed for this a time of 2 minutes. Subsequently the mixture was stirred for another hour at 80° C. and then cooled to room temperature.

The thus obtained polycondensation product of acrolein and formaldehyde in the molar ratio 1:3 was tested in concentrations of 100 ppm and 20 ppm on algae cultures. At 100 ppm within 3 days there occurred complete destruction of the algae, while at 20 ppm within this time there was observed a strong damage to the algae.

EXAMPLE 5

There were mixed in a 250 ml round bottom flask equipped with a stirrer 34.5 cc of acrolein (purity 96%, density 0.845)=0.5 mole, 72.6 cc of an aqueous formaldehyde solution (content 37%, density 1.116)=1 mole and 34 cc of allyl alcohol (density 0.854)=0.5 mole and the mixture treated with 0.5 cc of piperidine at room temperature. Within 4 minutes the temperature of the reaction mixture increased to 78° C. Subsequently the mixture was stirred for another hour at 80° C. and then cooled to room temperature.

The polycondensation product of acrolein and formaldehyde in the molar ratio 1:2 thus produced in the presence of allyl alcohol was tested on algae cultures in concentrations of 100 ppm, 20 ppm and 5 ppm. Within 3 to 4 days there occurred a complete destruction of the algae at 100 ppm and 20 ppm and at 5 ppm there was obtained a satisfactory damage to the algae.

EXAMPLE 6

There were present in a 250 ml round bottom flask provided with stirrer and reflux condenser 34.5 cc of formamide (density 1.133)=0.5 mole and 0.5 cc of piperidine and the mixture heated to 80° C. There was dropped in with stirring a homogeneous mixture of 34.5 cc of acrolein (purity 96%, density 0.845)=0.5 mole and 72.6 cc of an aqueous formaldehyde solution (content 37%, density 1.116)=1 mole within one minute while maintaining a highest temperature of 80° C. Subsequently the mixture was stirred for another hour at 80° C. and then cooled to room temperature.

The thus obtained polycondensation product of acrolein and formaldehyde in the molar ratio 1:2 produced in the presence of formamide was tested in concentrations of 100 ppm, 20 ppm and 5 ppm on algae cultures. Within 3 to 4 days there occurred at 100 ppm and 20 ppm complete destruction of the algae and at 5 ppm there was obtained a satisfactory damage to the algae.

EXAMPLE 7

There were present in a 250 ml round bottom flask equipped with stirrer and reflux condenser 31 grams of ethylene glycol=0.5 mole and 0.5 cc of piperidine and the mixture heated to 80° C. There was dropped in with stirring a homogeneous mixture of 34.5 cc of acrolein (purity 96%, density 0.845)=0.5 mole and 72.6 cc of an aqueous formaldehyde solution (content 37%, density 1.116)=1 mole within 1 minute, whereby the temperature did not exceed 80° C. Subsequently the mixture was stirred for another hour at 80° C. and then cooled to room temperature.

The thus obtained polycondensation product of acrolein and formaldehyde in the molar ratio 1:2 produced in the presence of ethylene glycol was tested in concentrations of 100 ppm, 20 ppm and 5 ppm on algae cultures. Within 3 to 4 days there occurred at 100 ppm and 20 ppm complete destruction of the algae and at 5 ppm there was obtained a satisfactory damage to the algae.

The entire disclosure of German priority application P 3205487.4 is hereby incorporated by reference.

What is claimed is:

1. A process of killing microorganisms or algae in an aqueous system comprising treating the aqueous system with a biocidally effective amount of a water soluble polycondensation product produced by condensation of acrolein and formaldehyde in the molar ratio between 1:1 and 1:10 in an aqueous or aqueous-organic medium.

2. A process according to claim 1 wherein there is employed 1 to 500 ppm of the polycondensation product.

3. A process according to claim 2 wherein there is employed 5 to 200 ppm of the polycondensation product.

4. A process according to claim 3 wherein there is employed 100 to 200 ppm of the polycondensation product.

5. A process according to claim 3 wherein there is employed 5 to 100 ppm of the polycondensation product.

6. A process according to claim 5 wherein there is employed 5 to 50 ppm of the polycondensation product.

7. A process according to claim 2 wherein the acrolein and formaldehyde are condensed in the presence of a water soluble alcohol or carboxylic acid amide.

8. A process according to claim 1 wherein the aqueous system contains algae, fungi, molds, or bacteria.

9. A process according to claim 1 wherein the molar ratio of acrolein to formaldehyde is between 1:2 and 1:4.

10. A process according to claim 9 wherein there is employed 1 to 500 ppm of the polycondensation product.

11. A process according to claim 10 wherein the acrolein and formaldehyde are condensed in the presence of a water soluble alcohol or carboxylic acid amide.

12. A process according to claim 11 wherein the alcohol or amide is a lower alkanol, lower alkanediol, lower polyalkylene glycol, allyl alcohol, formamide, acetamide, urea or caprolactam.

13. A process according to claim 12 wherein the acrolein and formaldehyde are condensed in the presence of allyl alcohol.

14. A process according to claim 12 wherein the acrolein and formaldehyde are condensed in the presence of formamide.

15. A process according to claim 1 wherein the acrolein and formaldehyde are condensed in the presence of a water soluble alcohol or carboxylic acid amide.

* * * * *